United States Patent [19]

Fehlauer

[11] Patent Number: 4,947,696

[45] Date of Patent: Aug. 14, 1990

[54] BELLOW PUMP FOR GAS TEST TUBE

[75] Inventor: Kai-Uwe Fehlauer, Lubeck, Fed. Rep. of Germany

[73] Assignee: Drägerwerk Aktiengesellschaft, Lübeck, Fed. Rep. of Germany

[21] Appl. No.: 343,788

[22] Filed: Apr. 26, 1989

[51] Int. Cl.⁵ .............................................. G01N 1/14
[52] U.S. Cl. ............................... 73/864.34; 73/863.84; 73/863.86
[58] Field of Search ........... 73/864.35, 864.73, 863.83, 73/863.84, 863.86, 864.34

[56] References Cited

U.S. PATENT DOCUMENTS

| | | | |
|---|---|---|---|
| 3,446,600 | 5/1969 | Wachter et al. | 73/864.34 X |
| 3,759,106 | 9/1973 | Wächter et al. | 73/864.34 |
| 3,782,198 | 1/1974 | Wächter et al. | 73/864.34 |
| 3,861,217 | 1/1975 | Rabenecker et al. | 73/864.34 |
| 3,901,084 | 8/1975 | Breilsford | 73/864.35 |
| 4,574,647 | 3/1986 | Molt | 73/864.34 |
| 4,610,171 | 9/1986 | Nason | 73/864.73 X |

FOREIGN PATENT DOCUMENTS 1007523 10/1957 Fed. Rep. of Germany .
2843651 4/1980 Fed. Rep. of Germany .
3330578 3/1985 Fed. Rep. of Germany .

Primary Examiner—Tom Noland
Attorney, Agent, or Firm—McGlew & Tuttle

[57] ABSTRACT

A pump for gas test tubes comprising two handle plates interconnected at respective ends by bellows and which are spring-biased in the direction of a suction sampling stroke. An inlet valve is constructed for the space enclosed in the bellows to insure that only non-manipulatable suction strokes with an exactly defined volume can be executed. For this purpose the inlet valve is arranged in the intake duct between the gas test tube and the interior of the bellows and closes in the direction toward the interior of the bellows. It can be opened by actuating the handle plates for the initiation of a complete sampling stroke and it remains open during the sampling stroke.

15 Claims, 2 Drawing Sheets

BELLOW PUMP FOR GAS TEST TUBE

BACKGROUND OF THE INVENTION

1. Field of the Invention

The invention relates, in general, to gas testing devices and, in particular, to a new and useful pump for gas test tubes. A similar bellows pump is known from German Pat. No. 10 07 523. Herein the gas to be tested is sucked through the gas test tube by means of a suction pump having the shape of a bellows pump, the gas escapes through the outlet valve on the side opposite the test tube when the bellows handle plates are pressed together, and it is sucked through the gas test tube when the handle plates are pressed back into their starting position by means of the force of a spring. This known bellows pump has the disadvantage that the volume of the sample is only consistent when the pump stroke is completed, it is not consistent, however, if the handle plates are e.g. not pressed together completely or are disposed at an angle due to carelessness. Furthermore, once the stroke is completed it is not possible to control whether an equalization of pressure has taken place and therefore whether the intended gas volume was sucked completely through the gas test tube before the next pump stroke can be executed.

German Pat. No. 33 30 578 shows an air feed pump whose device housing has the shape of a handle and the suction element is a bellows with a bottom plate. The bottom plate is connected to a centrally guided control rod, which is spring-biased in the direction of the suction stroke and can be arrested. The arresting takes place in the evacuated position of the bellows. Once the control rod is released, a complete suction stroke is executed. A window is provided in the device housing, in which a mark becomes visible with the end of the suction stroke. This air conveyor has a complicated design, however, and only allows for a limited pump stroke when operated with one hand. If the bellows is not pressed together completely, the control rod cannot be arrested and an undefined suction stroke can be executed, if, e.g., the air conveyor slips from the operator's hand while being operated with one hand. The mark in the window merely shows the final position of the bellows and does not allow for any control of whether the air is sucked through the gas test tube completely.

German Pat. No. 28 43 651 describes a function-testing device for a gas test device. It comprises a cylindrical housing with a colored jump-type membrane and a dispersion disc arranged correspondingly. The testing device is slipped onto the free end of the gas test tube, the sample air entering through a second opening at the cylindrical housing. For the determination of the pressure in the air flow, the open end is closed. The vacuum generating in the housing results in a movement of the jump-type membrane in the direction of the dispersion disc and therefore the color code becomes visible. A disadvantage of this device is that it has to be slipped onto the test tube as a separate component and that it requires special handling.

SUMMARY OF THE INVENTION

According to the invention provides a bellows pump that only complete, non-manipulatable suction strokes with an exactly defined volume can be executed.

According to the invention an inlet valve is disposed in the intake duct between the gas test tube and the interior of the bellows. The intake valve closes in a direction of the bellows interior and can be opened for the execution of a complete sampling stroke by operating the handle plates. This valve opens the gas flow through the gas test tube and therefore during the beginning of the sampling stroke only if the correct stroke volume for the sample was pre-determined by a previous complete pressing together of the handle plates. If the handle plates are not pressed together completely, the inlet valve is closed after the release, the gas flow is interrupted and the handle plates remain in an intermediate position.

Claim 2 describes an advantageous embodiment of the valve. Opposite the valve seat of the inlet valve a second valve seat is arranged in the intake duct, which serves as a non-return valve together with the valve plate of the inlet valve. It blocks the gas flow between the interior of the bellows and the intake duct in the period of time during which the handle plates are pressed together by the operator. This is to ensure that the gas escapes completely through the outlet valve in the bottom handle plate and that it does not return to the gas test tube through the intake duct.

In the end range of the tensioning stroke the valve is held open by a control pin, which can be actuated by means of a pump element movable in the stroke direction and which removes the valve plate from its seat.

It is advantageous to use the stay of a shear-joint serving for the parallel guidance of the handle plates as the pump element movable in the stroke-direction. By means of the lever effect the pump stroke of the initiation phase is reduced to the smaller stroke of the switch pin and the valve at the end of the stay where the switch pin engages, and an equalization is achieved without any major effort.

Furthermore, the shear joint guarantees a constant compression of the bellows volume and prevents the handle plates from moving toward one another at an angle.

It can be advantageous to arrange the pump element movable in the stroke-direction as a control pin connected to the lower handle plate.

It is favorable to make the inlet valve a marginal operation valve or marginal flow valve, which closes when the air flow exceeds the limit value determined by the inherent resistance of the gas test tube. The operation is based on the fact that between the filling of the gas test tube and the valve there is a gas volume that totals the shape of the hollow test tube end, and the reception and the intake duct. At the beginning of every suction stroke the gas volume is sucked into the bellows as a high initial flow with a jerk. Only then does the sampling flow occur, which is determined by the resistance of the test tube filling and which is much smaller.

If the handle plates are pressed together insufficiently, the high initial flow leads to the closing of the valve. The gas flow in the intake duct is interrupted and the handle plates remain in the intermediate position. When the handle plates are pressed together completely, however, the valve is moved into the open-position by means of a switch pin. During the following transport stroke the valve is kept open by the switch pin during the high initial flow until the air flow has exceeded the limit value and becomes the sampling flow. During the continuation of the transport stroke the valve remains in the open position without aid.

A further advantageous arrangement for keeping the inlet valve in the open-position during the sampling stroke is to lock the switch pin with a pressure-sensitive locking lever which is activated by the vacuum growing in the interior of the bellows. The lock is triggered off only once the sampling stroke has been executed and an equalization of pressure has taken place in the interior of the bellows.

A further embodiment is an inlet valve with a mechanically locked switch pin. When the handle plates are pressed together completely the switch pin and therefore the valve are moved into the open-position and the switch pin is arrested by means of a catch. It can be released by means of a pulling mechanism at the end of the sampling stroke.

It is advantageous to provide the bellows pump with a mark reacting to the pressure in the intake duct which indicates the end of a sampling cycle by showing the equalization of pressure after the end of the mechanical suction stroke. At the same time the action of the indicator mark provides a rough operation control of the bellows during the suction stroke.

An advantageous embodiment of the indicator mark is the execution as a jump-type membrane below a translucent dispersion disc.

Accordingly, it is an object of the invention to provide an improved pump which is connectable to a gas-sampling tube and which is constructed to operate so as to provide a full gas sampling stroke to effect an exactly defined gas volume for testing.

A further object of the invention is to provide a bellows-operated gas pump or collecting gas samples which includes handle members which are movable relative to each other and which are connected together by bellows to enclose an interior which has an inlet connected to the gas sampling tube and which is provided with a valve in the interior which is maintained in an open position during an entire stroke and cannot close until the complete stroke is effected and which will be positionable in a closed position after the stroke is completed.

A further object of the invention is to provide a bellows-operated pump for gas testing tubes which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

DETAILED DESCRIPTION OF THE DRAWINGS

Figure 1:
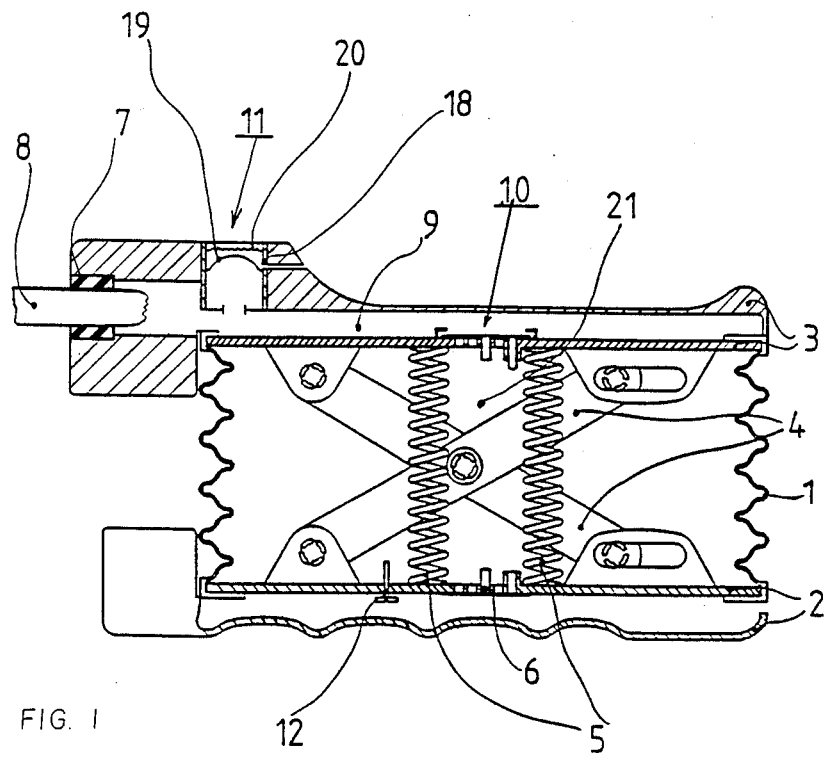
FIG. 1 is a longitudinal section through a bellows pump with the bellows being fully aerated and constructed in accordance with the invention.

Referring to the drawings, in particular, the invention embodied therein in FIG. 1 comprises a bellows pump generally designated 1 having handles 2 and 3 which are movable relative to each other and which may draw a gas sampling air through a testing tube 8 which is positioned in a reception area 7 through an intake duct 9 and an inlet valve 10 as to pull in a testing sample in the interior 21 of the bellows and which will operate to insure that a complete sampling stroke is effected while the inlet valve remains open during the sampling stroke.

The bellows pump represented in FIG. 1 comprises an elastic bellows 1 made from gas-impenetrable material and it has handle plates 2 and 3. The handle plates 2 and 3 are guided parallel by means of a shear or pivot joint of cross links 4. Two helical springs 5 are arranged inside the bellows and force or bias the bellows into the extended position. The lower handle plate 2 carries the outlet valve 6, through which the air in the interior 21 of the bellows can escape when the bellows 1 is compressed. The upper handle plate 3 has a reception 7 for the test tube 8, a valve 10 arranged in the intake duct, which valve is described in more detail in FIG. 2, and the upper an indicator mark. The pump stroke is adjustable by means of the adjustment screw 12.

The indicator mark comprises the housing 18 provided with a colored jump-type membrane 19 and a dispersion disc 20, which are both installed gas-tightly. A side of a jump-type membrane or flexible diaphragm 19 facing a dispersion disc 20 is connected to the intake duct 9. In its resting position the jump-type membrane 19 is vaulted toward the dispersion disc 20, so that the colored jump-type membrane 19 can be seen by the operator. Due to the vacuum generated in the interior of the bellows 21, and during the transport stroke, the jump-type membrane 19 is moved away from the dispersion disc 20. The color of the jump-type membrane 19 can no longer be recognized by the operator. Once the handle plates 2 and 3 have reached their end position, it takes a while until an equalization of pressure has taken place in the interior of the bellows 21. Only then is the correct sampling volume achieved. This is marked by the appearance of the indicator mark when the jump-type membrane 19 returns to its resting position. Only now can a further pump stroke be started.

Figure 2:
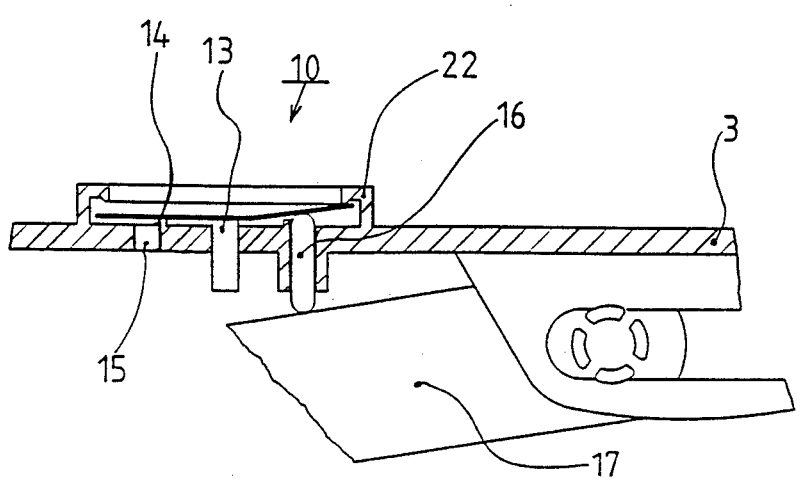
FIG. 2 is a longitudinal section through the marginal operation valve of the pump.

The marginal operation valve 10 shown in FIG. 2 comprises a rubber-elastic valve plate 13 resting on a support ring 14. The openings 15 in the upper handle plate 3 can be closed by means of the valve plate 13. During its resting position and with an even air flow during a sampling stroke the valve plate 13 rests on the support ring 14. The air enters the interior of the bellows pump through the openings 15. The openings 15 are arranged evenly spread around the outer circumference of the support ring 14.

If the handle plates 2 and 3 are pressed together only partially a brief release of an increased initial air flow takes place, which presses the valve plate 13 against the openings 15 and interrupts the air flow.

When the handle plates are pushed together completely, the switch pin 16 is operatively connected with the valve plate 13 by means of the stay 17. By means of the switch pin 16 the valve plate 13 is kept in the open-position until the air flow has slowed down to the stationary value of the sampling flow. Afterwards the valve plate remains in the horizontal open-position.

The second valve seat 22 and the valve plate 13 form a non-return valve blocking the gas flow from the interior of the bellows 21 into the intake duct 9 when the handle plates 2 and 3 are pressed together.

Figure 3:
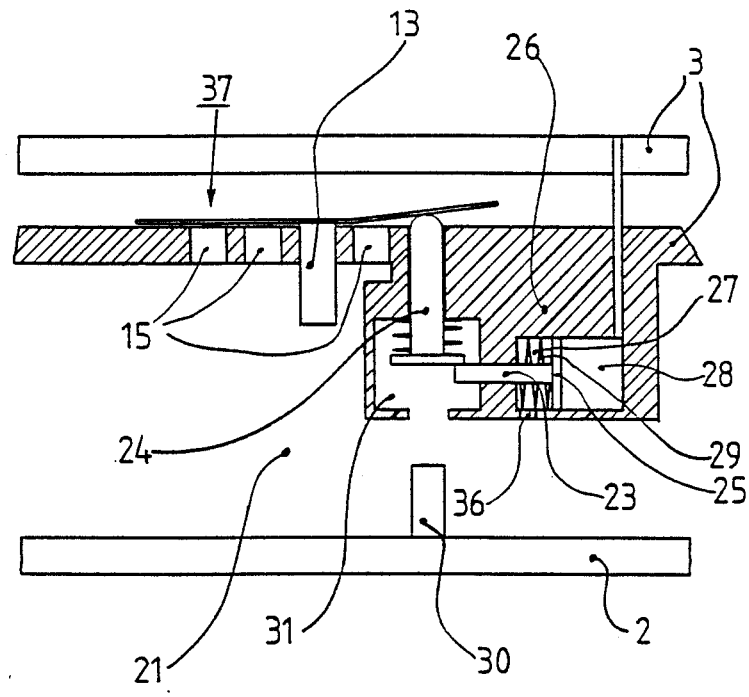
FIG. 3 is a longitudinal section through an inlet valve with a pneumatically actuated locking of the switch pin of another embodiment of the invention; and, FIG. 4 is a longitudinal section through an inlet valve with a mechanical locking of the switch pin of still another embodiment of the invention.

FIG. 3 shows an inlet valve 37 with a switch pin 24 that can be arrested by means of a catch lever 23. The catch lever 23 is connected to a piston 25 which is arranged gas-tightly and freely movable inside the control chamber 27. The control chamber 27 is arranged above an opening 36 connected to the interior of the bellows 21. Atmospheric pressure prevails in the equalizing chamber 28.

In the resting position the catch lever 23 is pushed into its end position due to the force of the readjusting spring 29. The switch pin 24 is released. When the handle plates 2 and 3 are pressed together completely, the switch pin 24 is actuated by means of a control pin 30 and the valve plate 13 is moved into the open-position. After the release of the handle plates 2 and 3 a vacuum is generated in the interior of the bellows 21 and via the opening 36 in the control chamber 27, said vacuum pressing the piston 25 against the readjusting spring 29 and relocating the catch lever 23 into the chamber 31. The switch pin 24 is locked. Once the sampling stroke and the consequent equalization of pressure are completed, the catch lever 23 returns into the resting position by means of the readjusting spring 29 and the switch pin 24 is released.

Figure 4:
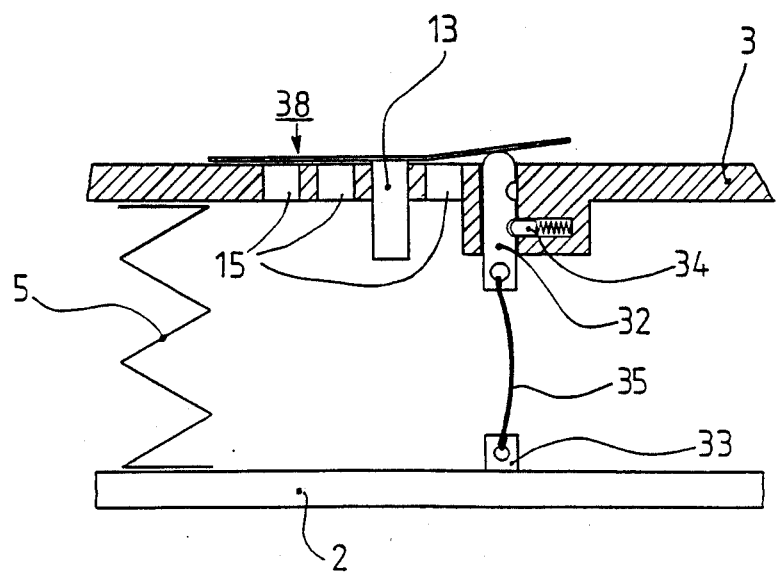

FIG. 4 shows an embodiment of the inlet valve 38 with a mechanical locking means for the switch pin 32. When the handle plates 2 and 3 are pressed together completely, the switch pin 32 is actuated by means of the control pin 33 and the valve plate 13 is moved into the open-position. The switch pin 32 is kept in this position by means of a catch device 34 and it is moved back into the starting position by means of a pulling device 35 once the sampling stroke is completed.

While specific embodiments of the invention have been shown and described in detail to illustrate the application of the principles of the invention, it will be understood that the invention may be embodied otherwise without departing from such principles.

What is claimed is:

1. A pump for connection to gas test tubes for effecting complete gas sampling intake strokes, comprising two handle plates, a bellows connected between said handle plates and defining a gas space between said handle plates and said bellows, the handle plates being mounted for movement in opposite directions relative to each other and between first and second positions corresponding to complete expansion and compression of the bellows respectively, means biasing said handle plates in a direction of movement towards the first position which expands the bellows and thereby effects a sampling stroke, an intake passage connected into said gas space and having a gas test tube connection, an intake valve in said intake passage between said gas test tube connection and said gas space, means mounting said intake valve closing the intake passage in a direction towards said gas space, intake valve actuating means connected with at least one of said handle plates and arranged to open said intake valve sufficiently for enabling the initiation of a complete gas sampling stroke and for maintaining said inlet valve open during the gas sampling stroke only on completion of movement of the handle plates to the second position corresponding to complete compression of the bellows.

2. A bellows pump according to claim 1, wherein said intake valve includes first and second valve seats, a valve member between said seats, movable in opposite directions to close respective ones of said seats, and providing an inlet in one direction and a non-return valve in an opposite direction.

3. A pump according to claim 2, wherein said inlet passage has an opening therethrough from said passage into the interior of said bellows to said gas space, a plate overlying said opening and closing said opening, a plate valve being movable between said first seat comprising said opening through said inlet passage and said second seat where it acts as a one-way valve, said handle plates being held by pivotal stay members extending therebetween and including a switch pin acting on said valve plate and extending into said gas space against said stay member and being actuated thereby to hold said valve plate in an open position.

4. A bellows pump according to claim 1, wherein said intake valve includes a plate member, said inlet passage having an opening leading from said passage into said gas space which is covered by said plate member, a switch pin mounted in said inlet and being movable against said plate to lift said plate to open said inlet and a catch lever mounted in said pump and being movable to engage and hold said switch pin to hold said valve in an open position during operation of said pump.

5. A pump construction for sampling a gas withdrawn from a test tube, comprising first and second aligned hand plates, bellows mean interconnecting respective ends of said plates and enclosing a gas sample area between said plates and said bellows means, said bellows means biasing said plates to a separated position, inlet means connected to the test tube and having a valved opening extending into said gas sample area, guide means positioned in the sample area for guiding said first and second handle plates toward and away from each other to effect a pumping stroke and a discharge stroke, an outlet for discharging the sample gas connected out of the gas sample area, said inlet means including a valve seat opening into said gas sample area from the test tube, a valve member closeable on said valve seat to close off the opening and control means disposed between said first and second hand plate positioned to prevent said valve member from closing the opening when said hand plates are separated from each other by a predetermined amount.

6. A pump construction according to claim 5, wherein said control means includes a rigid member carried by one of said hand plates and engageable with said valve member to lift said member off said opening when said hand plates are in a fully separated position in which a complete sample has been taken.

7. A pump construction according to claim 5, wherein said valve member comprises a valve plate, said valve seat comprising an upstanding support ring defined on one of said first and second hand plates and having the opening in said ring which is closed by said valve plate.

8. A bellows pump according to claim 7, including a switch pin mounted in one of said handle plates, a pressure-sensitive catch lever engageable with said switch pin to hold it in an open position and vacuum means acting on said catch lever to actuate said catch lever during a sampling stroke by the pressure within said bellows in said gas sample space, said switch pin being releasable by a re-adjusting spring at the end of the sampling stroke upon the equalization of pressure between the interior of said bellows in said ga sampling space and the exterior of said pump.

9. A bellows pump according to claim 5, including a switch pin slidable in one of said first and second hand plates in contact with said valve member to raise and lower said valve member and a catch device mounted in said hand plate and engageable with said switch pin to hold it in a position in which it opens said valve member, and a pulling device for pulling said switch pin back to a position in which said valve member is closed upon separation of said first and second hand plates.

10. A bellows pump according to claim 9, wherein said indicator comprises a jump-type membrane arranged within said inlet means below a translucent dispersion disc.

11. A bellows pump according to claim 5, wherein said inlet means includes a chamber having a dispersion disc through which one can view said chamber from the exterior, and including a jump-tight membrane in said chamber below said disc being movable between a position extending toward said disc to a position extending away from said disc and providing a color which is visible through said disc when said membrane is positioned against said disc to indicate the end of a sampling stroke.

12. A bellows pump according to claim 5, including a visually apparent indicator associated with said inlet means for indicating the pressure in said inlet.

13. A pump construction according to claim 5, wherein said guide means includes a pivotal lever member, said control means comprising a switch pin engaged on said lever member and being movable upon opening of said first and second hand plates to a space part position to contact said valve member and to lift said valve member off said opening.

14. A pump construction according to claim 5, including stroke adjustment means for limiting the stroke of said first and second handle members relative to each other, said biasing means including coil springs arranged between said first and second hand plates, said guide means including cross link members totally interconnected at their intermediate portions and having ends connected to respective first and second hand plates.

15. A pump according to claim 5, wherein said control means includes a switch pin movable toward and away from said valve member, control member defined adjacent said switch pin and having a control piston movable therein and biased by spring means away from engagement with said switch pin and including means for applying pressure to said equalizing chamber to act on said piston to engage it against said switch pin and hold it in an open position when a sampling has been fully achieved.

* * * * *